United States Patent [19]
Vignaud et al.

[11] Patent Number: 5,261,907
[45] Date of Patent: Nov. 16, 1993

[54] INTERCONNECTING DEVICE ABLE TO LOCK SPINAL OSTEOSYNTHESIS FASTENERS

[76] Inventors: Jean L. Vignaud, 10 impasse Francois Audouin, 33400 Talence; Gilles Missenard, 94-96 quai Louis Blériot, 75016 Paris; Philippe Lapresle, 32 boulevard Victor Hugo, 92200 Neuilly Sur Seine; Jean F. Sacriste, 5 square Maurice Ravel La Chapelle Forestiére, 33115 Pyla Sur Mer, all of France

[21] Appl. No.: 883,863
[22] Filed: May 15, 1992
[51] Int. Cl.$^5$ .............................. A61B 17/56
[52] U.S. Cl. ........................ 606/60; 606/61
[58] Field of Search ............ 606/53, 61, 57, 58, 606/59, 72, 73; 128/69; 403/362

[56] References Cited

U.S. PATENT DOCUMENTS

| | | | |
|---|---|---|---|
| 3,242,922 | 3/1966 | Thomas | 606/61 |
| 3,865,105 | 2/1975 | Lode | 606/61 |
| 4,773,402 | 9/1988 | Asher | 606/61 |
| 4,805,602 | 2/1989 | Puno | 606/61 |
| 4,957,495 | 9/1990 | Kluger | 606/61 |
| 5,005,562 | 4/1991 | Cotrel | 606/59 |
| 5,042,982 | 8/1981 | Harms | 606/61 |
| 5,067,955 | 11/1991 | Cotrel | 606/61 |
| 5,092,867 | 3/1992 | Harms | 606/61 |
| 5,096,327 | 3/1992 | Ruland | 403/362 |
| 5,129,899 | 7/1992 | Small | 606/61 |

FOREIGN PATENT DOCUMENTS

| | | |
|---|---|---|
| 0348272 | 12/1989 | European Pat. Off. . |
| 0350925 | 1/1990 | European Pat. Off. . |
| 0383992 | 8/1990 | European Pat. Off. . |
| 3807335 | 9/1989 | Fed. Rep. of Germany . |

Primary Examiner—Michael A. Brown
Attorney, Agent, or Firm—Roylance, Abrams, Berdo & Goodman

[57] ABSTRACT

The invention concerns an interconnecting device able to lock two spinal osteosynthesis fasteners comprising an osseous fixation section formed by a screw, a bent-back plate or similar device and a body for fixing an integralization rod formed by a diapason head receiving both said rod and a locking screw, said interconnecting device being constituted by two annular elements able to be each externally attached onto one of the diapason heads, each annular element comprising an external locking rod able to slide into the clamping collar, the two clamping collars of the device being screwed down by a common screw traversing said collars.

16 Claims, 3 Drawing Sheets

FIG_1.

FIG_2_

5,261,907

INTERCONNECTING DEVICE ABLE TO LOCK SPINAL OSTEOSYNTHESIS FASTENERS

FIELD OF THE INVENTION

This invention relates to a device able to interconnect and lock in a particular position two spinal osteosynthesis fasteners.

BACKGROUND OF THE INVENTION

The invention concerns more particularly but not exclusively spinal osteosynthesis devices of the type comprising a rod housed and locked in a certain number of fasteners constituted by an osseous anchorage section formed by a screw or bent-shaped plate and a rod fixing body constituted by a diapason-shaped head housing between its two branches said rod which is locked by means of an attachment screw housed in an internal screw thread fitted on the internal faces opposite said branches.

Usually, for example in the case where one vertebra of the spine is fractured, two osteosynthesis rods are fixed in parallel on both sides of the spine with the aid of fasteners secured to certain vertebrae.

This device is completed by transversal renderedintegral and traction devices interconnecting the two rods, generally constituted by transversal rods interconnecting hooks engaged on the two rods.

These devices are not practical to install and are of a type which may twist the rods owing to the traction they could exert on the latter.

SUMMARY OF THE INVENTION

The object of the invention is in particular to provide a device for rendering integral in transversal traction such osteosynthesis devices, said devices being of more simple design, easier to install and more effective.

With this aim in mind, the purpose of the invention is to provide an interconnecting device able to lock two spinal osteosynthesis fasteners, said fasteners comprising an osseous fixation section formed by a screw, a bent-shaped plate or similar device and body for fixing an integralization rod formed by a diapason head housing both said rod and the locking screw, wherein it comprises two annular elements each able to be externally attached onto one of the diapason heads, each annular element comprising one external locking rod able to slide into a clamping collar, said two clamping collars of the device being screwed down by a common screw traversing said collars.

Each annular element attached onto a diapason head is locked on the latter when screwing down the locking screw of the interconnecting rod of the fasteners, the purpose of this operation being to spread apart the branches of the diapason and thus lock the annular element surrounding the diapason head.

Next, the external head of each annular element is adjusted via sliding inside its collar, the correct position being found for the two external rods and a simple screwing down of a single screw locks the two clamping collars.

The traction forces of the integralization device are thus exerted directly on the fasteners and no longer on the interconnecting rods between two fasteners and the various degrees of freedom of the locking rods of the annular elements and of the clamping collars allows for considerable flexibility as regards the positioning of the annular elements on the diapason heads, irrespective of their possible position or orientation.

The invention is also applicable to the interconnecting between two fasteners disposed on one given side of the spine and belonging to two osteosynthesis devices of the type mentioned above and disposed with one being an extension of the other, the device of the invention being mounted between the two extremity fasteners.

BRIEF DESCRIPTION OF THE DRAWINGS

Other characteristics and advantages shall appear more readily from a reading of the following description of one embodiment of the device of the invention, this description being given solely by way of example and with reference to the accompanying drawings on which.

DETAILED DESCRIPTION OF THE PREFERRED EMBODIMENTS

Figure 1:
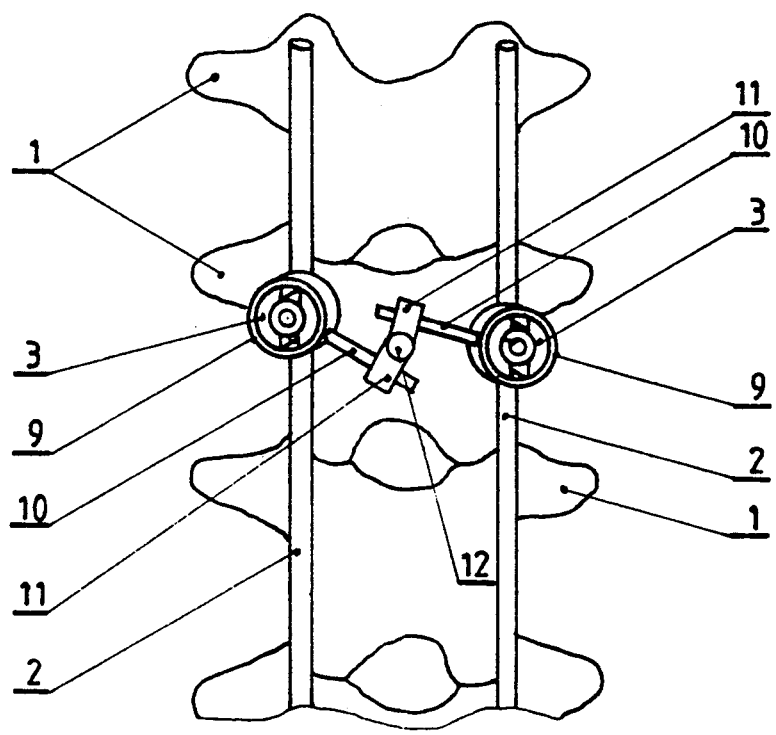
FIG. 1 shows an implantation on a spine of a spinal osteosynthesis device including the present invention.

FIG. 1 shows at 1 vertebrae provided with a spinal instrument including on both sides of the spine one integralization rod 2 connecting a certain number of fasteners constituted by an osseous fixing portion formed by a screw or a bent back plate, and a head for receiving and locking said rod 2.

Figure 2:
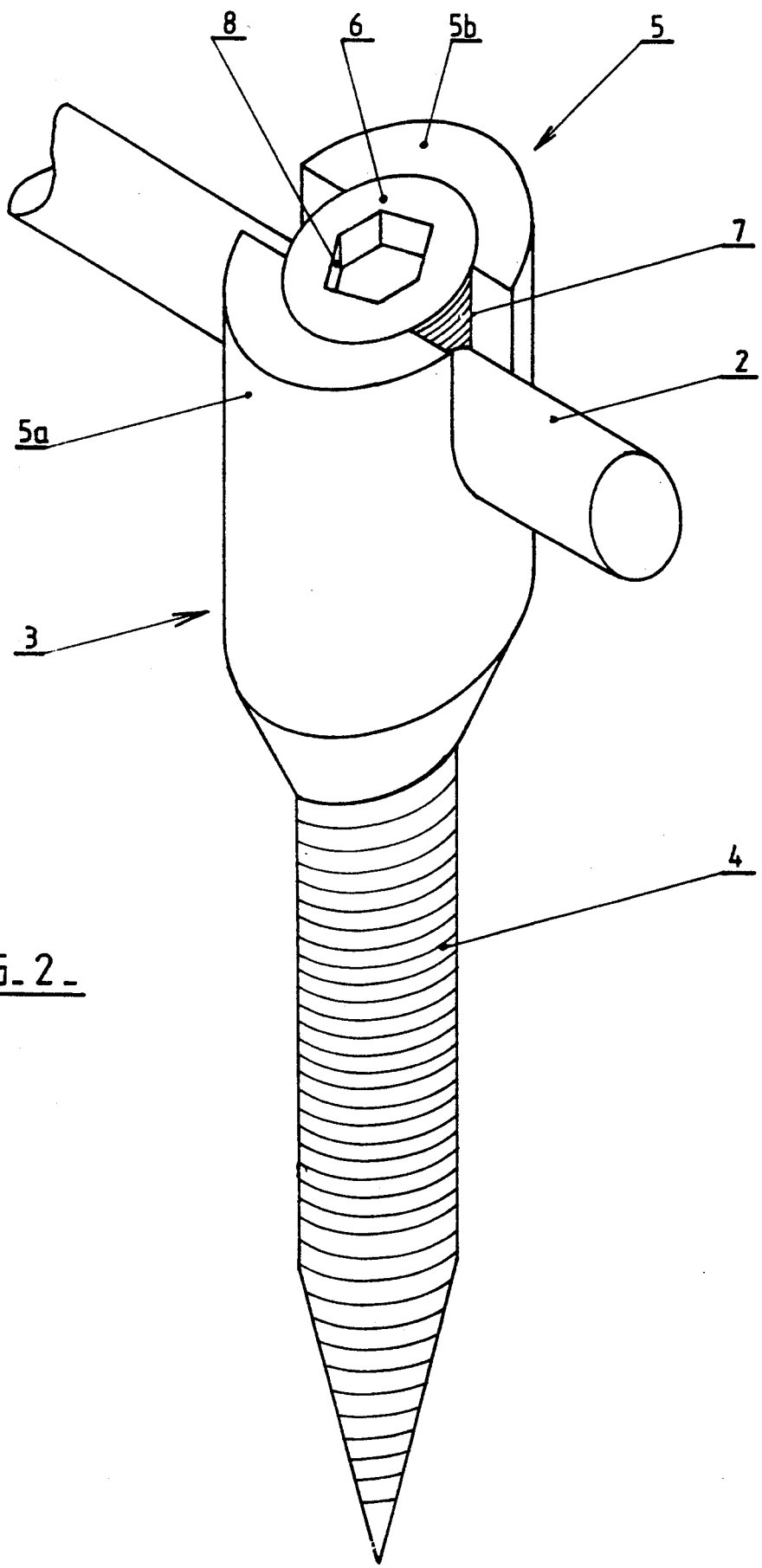
FIG. 2 shows a perspective and approximate front view of a known type of diapason head pedicular screw.

FIG. 1 shows for each rod 2 only one of these fasteners, for example a known type of a pedicular screw 3 detailed on FIG. 2.

This screw 3 includes a threaded osseous anchorage rod 4, a diapason-shaped cylindrical head 5 between the two branches 5a and 5b from which the rod 2 is kept locked by a locking screw 6 engaged between the branches 5a and 5b and screwed into an internal screw thread 7 provided on the internal faces opposite said branches. The locking screw 6 is provided on its upper face with a polygonal hollow indentation for receiving a wrench for locking the rod 2.

Such a device is well-known and is generally completed by an integralization and transversal traction device connecting the two rods 2, approximately parallel.

Figure 3:
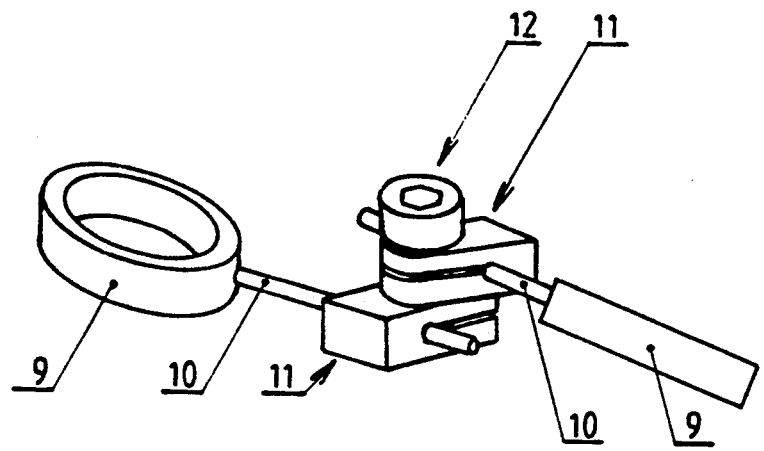
FIG. 3 is a perspective and approximate front view of a device conforming to the invention.
Figure 4:
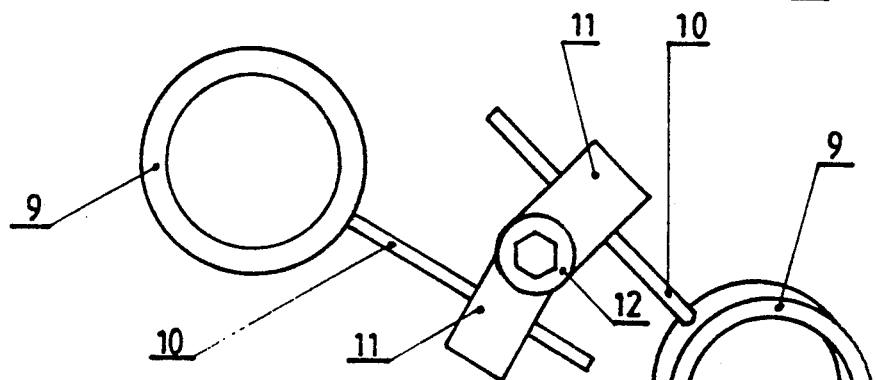
FIG. 4 is a top view of the device of FIG. 3.

In accordance with the invention, this integralization and transversal traction device, shown in more detail on the diagram of FIG. 1, is constituted according to a particular ambodiment appearing on FIGS. 3 and 4.

The device of the invention includes two annular elements 9 each externally provided with a locking rod 10 of a certain length. The axis of the rod 10 passes, for example, through the center of the auxiliary element 9 but could have any orientation inside the plane of the annular element and have any inclination with respect to this plane.

Each locking rod 10 is able to slide and can be locked in a clamping collar 11.

In the embodiment shown, the two clamping collars are superimposed and traversed by a common clamping screw 12 orthogonal to the two rods 10. The screw is for example an internal socket head screw similar to the screw 6.

Figure 5:
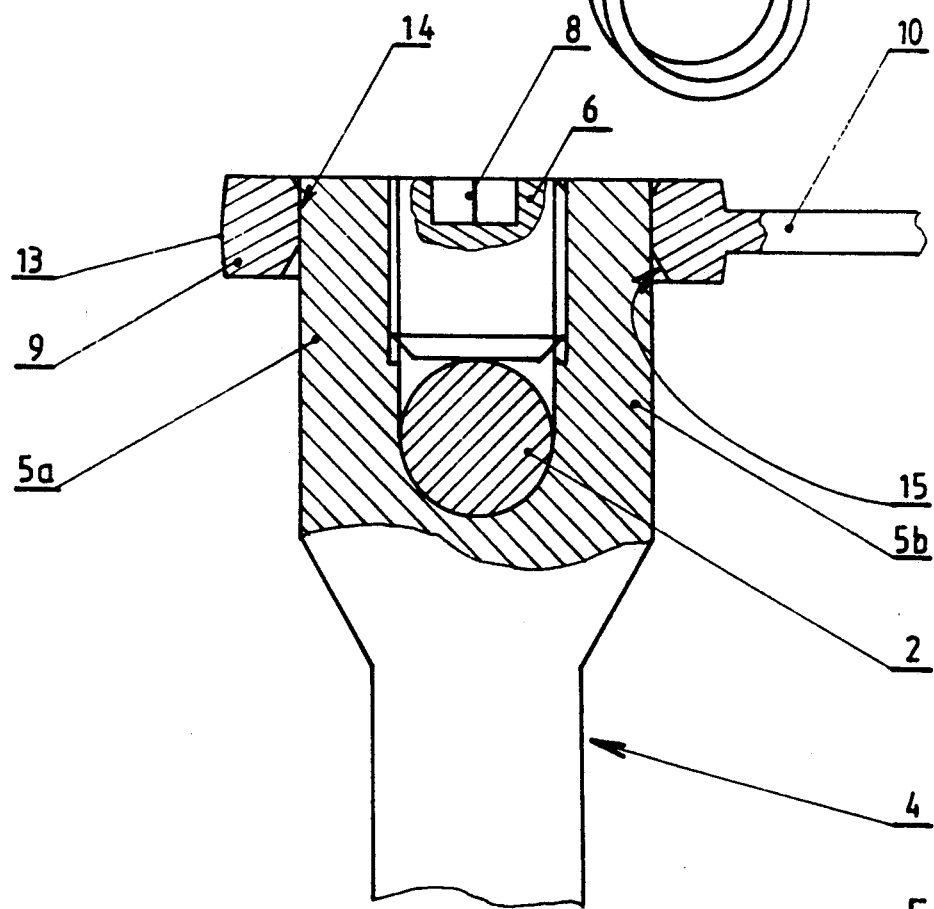
FIG. 5 is an axial partial cutaway view of a screw of the type of FIG. 2 to which an annular element of the device of FIGS. 3 and 4 is attached.

Each annular element 9 may comprise, as shown on FIG. 5, a convex external face, a cylindrical internal face 14 whose diameter corresponds to the external diameter of the heads 5 of the pedicular screws or other similar fasteners 3 and, at the side intended to be available on the heads of the fasteners (3), a chamfer 15 on the internal edge facilitating placing.

Each annular element 9 is attached to a head 5 prior to screwing down of the rod 2 by the screw 6, and is then locked in place by screwing down said screw 6, which tends to spread apart the branches 5a, 5b and thus lock said element 9.

The two elements 9 are placed between two fasteners 3 opposite, as shown on FIG. 1.

These two elements 9 may also be placed on two fasteners disposed on the same side of the spine. In this case, each fastener 3 is, for example, a pedicular screw for fixing the extremity of an interconnecting rod, the device of the invention thus embodying a coupling between the two osteosynthesis devices which are substantially in a line.

It is easy to place the elements 9 on the heads 5, regardless of the possible positions or orientations of said heads 5 by virtue of the various degrees of freedom of the connecting members between the two elements 9. In fact, each rod 10 may slide into a clamping collar 11 and rotates round its axis. Moreover, the two collars 11 are able to pivot with respect to each other by 360° around the common axis of the screw 12.

Once the rods 10 and collars have been correctly placed, a simple rotation of the sole screw 12 locks the unit in position.

Finally, the invention is not merely limited to the embodiment shown and described above but, on the contrary, covers all possible variants, especially as regards the fitting and possible disposition of the clamping collars 11.

As shown on FIGS. 2 and 3, instead of having a contact plane between the two clamping collars il perpendicular to the axis of the screw 12 it is possible to provide a contact plane forming with the axis of the screw 12 an angle different from the right angle, which would create additional positioning possibilities for the annular elements 9.

The elements of the device of the invention are, of course, contained in a biocompatible material approved for surgical implantation.

What is claimed is:

1. An interconnecting device for rigidly connecting together with a pair of spaced-apart fasteners, each fastener having an osseous fixation section formed by an attachment member, a diapason head receiving an integralization rod and a clamping screw engaged in said diapason head for securing the attachment member to the rod, said device comprising:
   first and second annular elements, each of said elements having an internal configuration conforming to an external configuration of the head of each fastener, respectively;
   first and second interlocking rods rigidly connected to said first and second annular elements, respectively; and extending outwardly therefrom;
   first and second clamping members slidably receiving terminal regions of said first and second interlocking rods, respectively; and
   a single screw means, extending through said first and second clamping members, for simultaneously clamping said members to said interlocking rods.

2. An interconnecting device according to claim 1 wherein said first and second clamping members are at least partially superimposed, and are relatively rotatable about a longitudinal axis of said single screw means enabling said interlocking rods to move in two parallel planes perpendicular to said longitudinal axis.

3. An interconnecting device according to claim 1 wherein said first and second clamping members are at least partially superimposed, and are relatively rotatable in a contact plane on each other, said contact plane forming an angle with a longitudinal axis of said single screw means not equal to 90 degrees.

4. An interconnecting device according to claim 1 wherein each of said annular elements comprises a cylindrical internal face ending in a chambered edge.

5. An interconnecting device according to claim 1 wherein each interlocking rod has a longitudinal axis passing through a center of the respective annular element.

6. An interconnecting device according to claim 1 wherein said first and second clamping members are at least partially superimposed, and are relatively rotatable in a contact plane on each other, said contact plane forming an angle with a longitudinal axis of said single screw means.

7. An interlocking device according to claim 1 wherein said first and second interlocking rods are rigid and are integral with said first and second annular elements, respectively.

8. An interlocking device according to claim 7 wherein said single screw means releasably clamps said first clamping member relative to said second clamping member.

9. A spinal osteosynthesis device, comprising;
   at least one integralization rod;
   first and second spaced-apart spinal fasteners, each of said spinal fasteners having an osseous fixation section formed by an attachment member, a diapason head receiving said at least one integralization rod and a clamping screw engaged in said diapason head for securing said integralization rod in said diapason head;
   first and second annular elements, each of said annular elements having an internal configuration conforming to an external configuration of the head of each fastener, respectively;
   first and second interlocking rods rigidly connected to said first and second annular elements, respectively, and extending outwardly therefrom;
   first and second clamping members slidably receiving terminal regions of said first and second interlocking rods, respectively; and
   a single screw means, extending through said first and second clamping members, for simultaneously clamping said members to said interlocking rods.

10. A spinal osteosynthesis device according to claim 9 wherein said first and second clamping members are at least partially superimposed, and are relatively rotatable about a longitudinal axis of said single screw means enabling said interlocking rods to rotate in two parallel planes perpendicular to said longitudinal axis.

11. A spinal osteosynthesis device according to claim 9 wherein said first and second clamping members are at least partially superimposed, and are relatively rotatable in a contact plane on each other, said contact plane forming an angle with a longitudinal axis of said single screw means not equal to 90 degrees.

12. A spinal osteosynthesis device according to claim 9 wherein each of said annular elements comprises a cylindrical internal face ending in a chambered edge.

13. A spinal osteosynthesis device according to claim 9 wherein each interlocking rod has a longitudinal axis extending through a center of the respective annular element.

14. A spinal osteosynthesis device according to claim 9 wherein said first and second clamping members are at least partially superimposed, and are relatively rotatable in a contact plane on each other, said contact plane forming an angle with a longitudinal axis of said single screw means.

15. A spinal osteosynthesis device according to claim 14 wherein said single screw means releasably clamps said first clamping member relative to said second clamping member.

16. A spinal osteosynthesis device according to claim 9 wherein said first and second interlocking rods are integral with said first and second annular elements, respectively.

* * * * *

UNITED STATES PATENT AND TRADEMARK OFFICE
CERTIFICATE OF CORRECTION

PATENT NO. : 5,261,907
DATED : November 16, 1993
INVENTOR(S) : Jean L. Vignaud et al.

It is certified that error appears in the above-identified patent and that said Letters Patent is hereby corrected as shown below:

On the title page, after and below item "[22] Filed: May 15, 1992",

Should appear item   [30] Foreign Application Priority Data

May 17, 1991 [FR] France ........ 91 06133 --

Signed and Sealed this

Seventeenth Day of May, 1994

Attest:

BRUCE LEHMAN

*Attesting Officer*   Commissioner of Patents and Trademarks